(12) United States Patent
Minnifield

(10) Patent No.: US 10,342,479 B1
(45) Date of Patent: Jul. 9, 2019

(54) SYSTEM AND METHOD FOR ASSESSING KNEE MOVEMENT

(71) Applicant: Measuring Every Day, Incorporated, Lexington, KY (US)

(72) Inventor: Franky Lydale Minnifield, Lexington, KY (US)

(73) Assignee: Measuring Every Day, Incorporated, Lexington, KY (US)

( * ) Notice: Subject to any disclaimer, the term of this patent is extended or adjusted under 35 U.S.C. 154(b) by 356 days.

(21) Appl. No.: 15/227,073

(22) Filed: Aug. 3, 2016

Related U.S. Application Data

(60) Provisional application No. 62/200,745, filed on Aug. 4, 2015.

(51) Int. Cl.
*A61B 5/00* (2006.01)
*A61B 5/107* (2006.01)

(52) U.S. Cl.
CPC .......... *A61B 5/4585* (2013.01); *A61B 5/1071* (2013.01)

(58) Field of Classification Search
CPC .............................. A61B 5/4585; A61B 5/1071
See application file for complete search history.

(56) References Cited

U.S. PATENT DOCUMENTS

| | | | |
|---|---|---|---|
| 1,571,261 A * | 2/1926 | Ginter | B43L 9/02 33/1 R |
| 4,583,555 A | 4/1986 | Malcom et al. | |
| 4,699,376 A | 10/1987 | Mattox et al. | |
| 6,436,058 B1 | 8/2002 | Krahner et al. | |
| 7,785,232 B2 | 8/2010 | Cole et al. | |
| 8,282,579 B2 | 10/2012 | Bright et al. | |
| 8,341,850 B2 | 1/2013 | Merchant | |
| 2006/0064044 A1 | 3/2006 | Schmehl | |
| 2007/0043308 A1 | 2/2007 | Lee | |

(Continued)

FOREIGN PATENT DOCUMENTS

WO 03/094729 A1 11/2003

OTHER PUBLICATIONS

Rehabilitation Knee Stretch Device for Knee Pain and Meniscus Injuries, www.mendmyknee.com/knee-pain/knee-joint-rehabilitation-therapy-device.php (downloaded Jan. 20, 2014).

*Primary Examiner* — Daniel L Cerioni
*Assistant Examiner* — Yasmeen S Warsi
(74) *Attorney, Agent, or Firm* — Stites & Harbison, PLLC; David W. Nagle, Jr.; James R. Hayne

(57) ABSTRACT

A system for assessing knee movement of an individual comprises: a goniometer with a central body portion; a first adjustable leg mounted for movement with respect to the goniometer to represent a lower leg measurement of the individual; a second adjustable leg mounted for movement with respect to the goniometer to represent an upper leg measurement of the individual; and a base board marked with indicia to measure a linear position of a heel of the individual when a knee of the individual is at maximum flexion. The distal end of the first adjustable leg and the distal end of the second adjustable leg are positioned on the base board, with the first adjustable leg and the second adjustable leg in a fixed position relative to the goniometer, to determine an angular measurement of the knee of the individual at maximum flexion by referencing indicia on the goniometer.

11 Claims, 4 Drawing Sheets

(56) References Cited

U.S. PATENT DOCUMENTS

| | | | |
|---|---|---|---|
| 2007/0266579 A1* | 11/2007 | Briscoe | A61B 5/1071 33/503 |
| 2008/0132818 A1 | 6/2008 | Livorsi | |
| 2012/0226199 A1 | 9/2012 | Noveau et al. | |
| 2016/0000369 A1* | 1/2016 | Minnifield | A61B 5/1072 600/595 |

* cited by examiner

SYSTEM AND METHOD FOR ASSESSING KNEE MOVEMENT

CROSS-REFERENCE TO RELATED APPLICATIONS

The present application claims priority to U.S. Patent Application Ser. No. 62/200,745 filed on Aug. 4, 2015, the entire disclosure of which is incorporated herein by reference.

BACKGROUND OF THE INVENTION

The present invention relates to a system and method for assessing knee movement, and, more particularly, the range-of-motion in a knee joint, for example, as part of post-operative physical therapy.

Knee-related injuries are one of the most common injuries in sports. Many knee injuries result in a ruptured or torn anterior cruciate ligament (ACL), one of the four major ligaments of the knee. Injury to the ACL is often remedied by reconstructive surgery, followed by several months of physical therapy and rehabilitation. In order to track changes in the range-of-motion of the knee, a goniometer is often used to directly measure the angle between the lower and upper leg when in flexion. A goniometer is a plastic or metal tool with two arms, usually no longer than twelve inches, with at least one of the arms mounted for rotation relative to the other arm about a central axis. This central axis is aligned with the axis of rotation of the knee, and the arms are aligned with the greater trochanter of the femur and the lateral malleolus of the fibula in order to take a measurement using a scale on a central body portion of the goniometer.

One of the significant problems with a typical goniometer is the dependence on accurately positioning the central axis and the arms of the goniometer in relation to the patient's knee. Exacerbating this issue is the desire to take a measurement quickly so that the patient can return their leg to a relaxed position. Some studies suggest that these errors can be anywhere between 5 and 10 degrees when taking repeated measurements. Furthermore, a typical goniometer can only be used in a clinical setting with the assistance of a therapist.

Thus, there remains a need for improved systems and methods for assessing knee movement.

SUMMARY OF THE INVENTION

The present invention is a system and method for assessing knee movement, and, more particularly, the range-of-motion in a knee joint, for example, as part of post-operative physical therapy. An exemplary system generally comprises: a goniometer; a first adjustable leg mounted for movement with respect to the goniometer; a second adjustable leg mounted for movement with respect to the goniometer; and a base board marked with indicia to measure a linear position.

In some embodiments, the goniometer is a typical goniometer well known in the art and includes a central body portion, a first leg extending away from the central body portion, and a second leg which is pivotally connected to the central body portion.

The adjustable legs are preferably aligned with and effectively serve as extensions of the two legs of the goniometer. It is contemplated, however, that in some alternate embodiments, the adjustable legs may replace the legs of the goniometer entirely. Regardless, each of the adjustable legs terminates in a distal end and includes a central channel defined along the longitudinal axis of the adjustable leg, thus allowing the distance between the distal ends of the respective adjustable legs and the central body portion of the goniometer to be adjusted to a desired length.

A clamping knob connects the goniometer and the adjustable legs by way of a pivot pin that extends from the clamping knob and through the goniometer, the first adjustable leg, and the second adjustable leg. A nut is connected to the pivot pin opposite the clamping knob, such that the goniometer, the first adjustable leg, and the second adjustable leg are positioned between the clamping knob and the nut. In this way, by loosening the clamping knob, each of the adjustable legs can slide relative to the goniometer along the length of the respective central channels defined by the adjustable legs, thus allowing for adjustments in the length of each adjustable leg relative to the goniometer. Similarly, each of the adjustable legs can rotate relative to the other adjustable leg about the pivot pin to any desired angular distance between the adjustable legs. When a desired position of the adjustable legs is achieved, the clamping knob is tightened, locking the adjustable legs in place relative to each other and the goniometer.

The system also includes a base board. The base board is an elongated member which is marked with indicia on its upper surface for linear measurements. In some embodiments, the base board also includes a heel stop removably attached to the base board at a distal end thereof.

In order to assess the knee flexion of an individual with the system of the present invention, measurements of the patient's lower leg and the patient's upper leg are taken. The first adjustable leg is positioned relative to the goniometer to represent the lower leg measurement, and the second adjustable leg is positioned relative to the goniometer to represent the upper leg measurement.

The patient then sits down and positions his or her leg on the base board in a "zero flexion position." The patient begins bending his knee, such that the foot slides along the upper surface of the base board until the knee is at maximum flexion, and the linear position of the heel at maximum flexion is marked on the base board.

The patient may now stand up or otherwise move away from the base board. The distal end of the first adjustable leg is positioned on the base board at the position of the heel at maximum flexion, and the distal end of the second adjustable leg is positioned on the base board at a position representing the total leg length of the patient. The two adjustable legs now approximately recreate the position of the patient's leg under maximum flexion, and once the position of the two adjustable legs is fixed relative to the goniometer, the goniometer can be used to determine an angular measurement of the knee of the individual at maximum flexion.

Advantageously, the system and method of the present invention provide a simple and accurate means of measuring the degree of flexion in the patient's knee. The patient is not required to hold his or her leg in maximum flexion while the angular measurement is taken. Rather, a simple linear measurement of maximum heel movement can be easily taken and later converted into an angular measurement by using the adjustable legs to simulate the patient's leg.

DETAILED DESCRIPTION OF THE INVENTION

The present invention is a system and method for assessing knee movement, and, more particularly, the range-of-motion in a knee joint, for example, as part of post-operative physical therapy.

Figure 1:
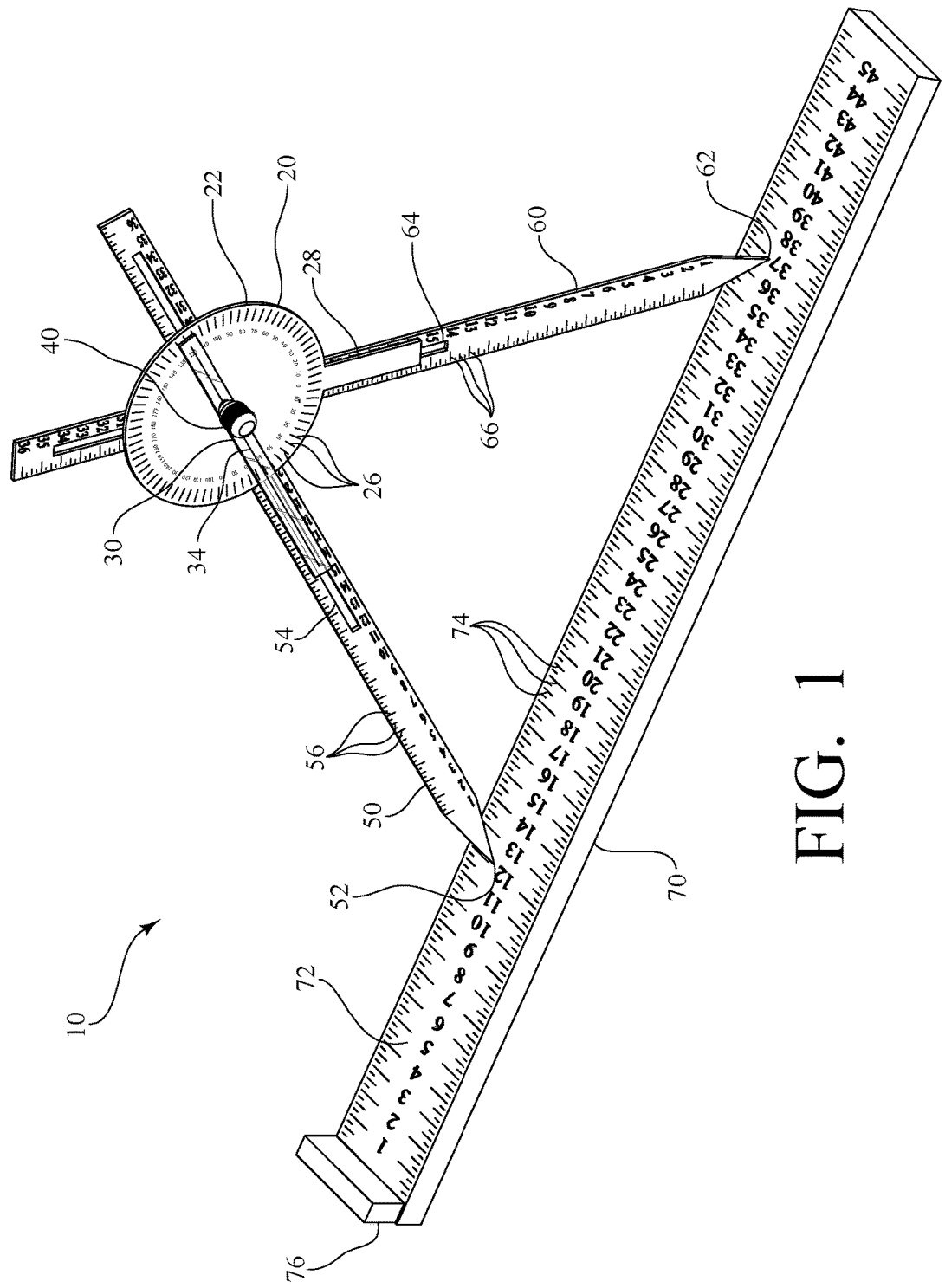
FIG. 1 is a perspective view of an exemplary system for assessing knee movement of an individual made in accordance with the present invention.
Figure 2:
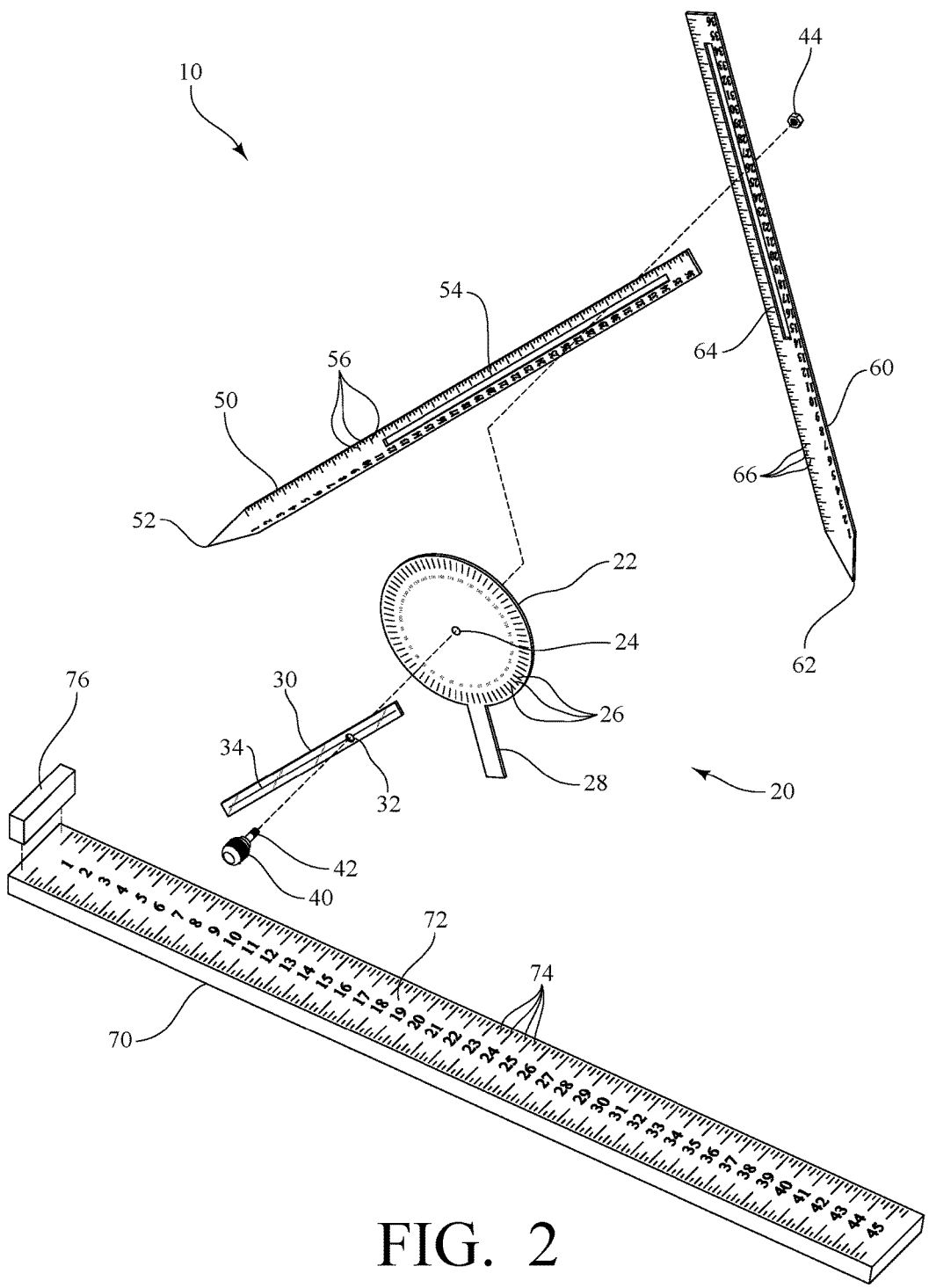
FIG. 2 is an exploded view of the exemplary system of FIG. 1.

As shown in FIGS. 1 and 2, an exemplary system 10 made in accordance with the present invention generally comprises: a goniometer 20; a first adjustable leg 50 mounted for movement with respect to the goniometer 20; a second adjustable leg 60 mounted for movement with respect to the goniometer 20; and a base board 70 marked with indicia 74 to measure a linear position.

The goniometer 20 is a typical goniometer well known in the art. For example, one such goniometer suitable for use in the system of the present invention is the EGM-422 EMI 12" Protractor Goniometer manufactured and distributed by Elite Medical Instruments of Fullerton, Calif. The goniometer 20 includes a central body portion 22 defining an axis hole 24 (FIG. 2), a first leg 28 extending away from the central body portion 22, and a second leg 30 which is pivotally connected to the central body portion 22. Specifically, the second leg 30 defines a pivot hole 32 (FIG. 2) that is aligned with the axis hole 24 defined by the central body portion 22, such that the second leg 30 can rotate about a pivot pin relative to the first leg 28, as further discussed below. In the exemplary embodiment shown in FIGS. 1 and 2, the first leg 28 is integral with and extends from the central body portion 22, which is marked with indicia 26 along its perimeter for angular measurements, and the second leg 30 includes a center line 34 which aligns with the indicia 26 on the central body portion 22 and thus allows for accurate measurements of the angle between the first and second legs 28, 30.

Referring still to FIGS. 1 and 2, the adjustable legs 50, 60 are preferably aligned with and effectively serve as extensions of the first and second legs 28, 30 of the goniometer 20. It is contemplated, however, that in some alternate embodiments, the adjustable legs 50, 60 may replace the legs 28, 30 of the goniometer 20 entirely. Regardless, each of the adjustable legs 50, 60 terminates in a distal end 52, 62 (which is preferably pointed). Each of the adjustable legs 50, 60 also includes a central channel 54, 64 defined along the longitudinal axis of the adjustable leg 50, 60, with each of the central channels 54, 64 partially overlapping the axis hole 24 of the central body portion 22. The central channels 54, 64 thus allow the distance between the distal ends 52, 62 of the adjustable legs 50, 60 and the central body portion 22 of the goniometer 20 to be adjusted to a desired length, as further discussed below. To this end, in this exemplary embodiment, each of the adjustable legs 50, 60 is marked with indicia 56, 66 along its length for linear measurements.

Referring still to FIGS. 1 and 2, the goniometer 20 and adjustable legs 50, 60 are connected by a clamping knob 40. More specifically, as shown in FIG. 2, a pivot pin 42 extends from the clamping knob 40 and through: (i) the pivot hole 32 defined by the second leg 30 of the goniometer 20, (ii) the axis hole 24 defined by the central body portion 22 of the goniometer 20, (iii) the central channel 54 defined by the first adjustable leg 50, and (iv) the central channel 64 defined by the second adjustable leg 60.

As shown in FIG. 2, a nut 44 is connected to the pivot pin 42 opposite the clamping knob 40, such that the second leg 30 of the goniometer, the central body portion 22 of the goniometer 20, the first adjustable leg 50, and the second adjustable leg 60 are positioned between the clamping knob 40 and the nut 44. In this way, by loosening the nut 44, each of the adjustable legs 50, 60 can slide relative to the goniometer 20 along the length of the respective central channels 54, 64 defined by the adjustable legs 50, 60, thus allowing for adjustments in the length of each adjustable leg 50, 60 relative to the goniometer 20. Similarly, each of the adjustable legs 50, 60 can rotate relative to the other adjustable leg 50, 60 about the pivot pin 42 to any desired angular distance between the adjustable legs 50, 60. When a desired position of the adjustable legs 50, 60 is achieved, the clamping knob 40 is tightened, locking the adjustable legs 50, 60 in place relative to each other and the goniometer 20.

Referring still to FIGS. 1 and 2, as mentioned above, the system also includes a base board 70. The base board 70 is an elongated member which is marked with indicia 74 on its upper surface 72 for linear measurements. In this exemplary embodiment, the base board 70 also includes a heel stop 76 removably attached to the base board 70 at a distal end thereof, as further discussed below.

Figure 3:
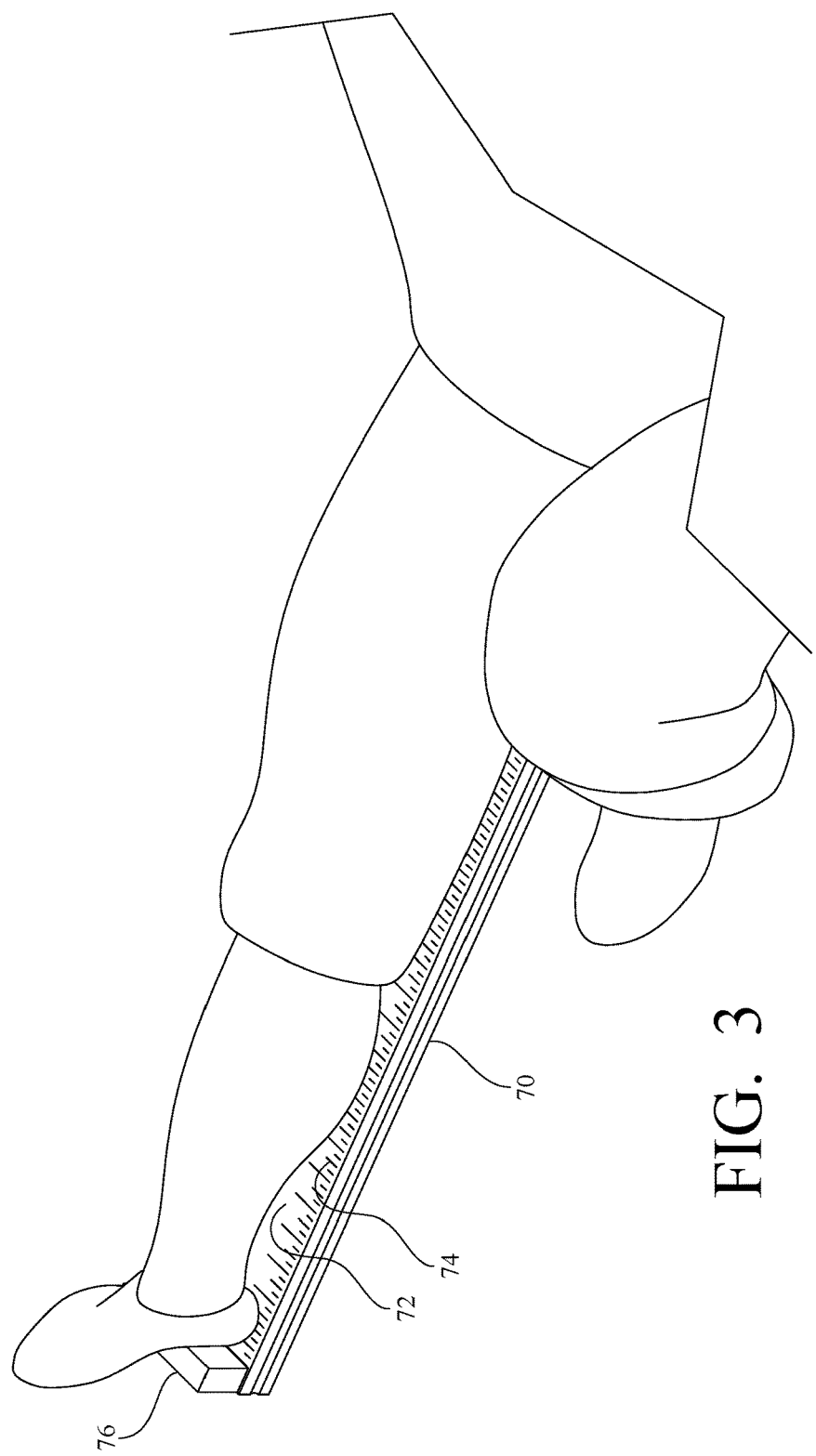
FIG. 3 is a perspective view of a portion of the exemplary system of FIG. 1 in use, with a patient's leg in a zero flexion position.
Figure 4:
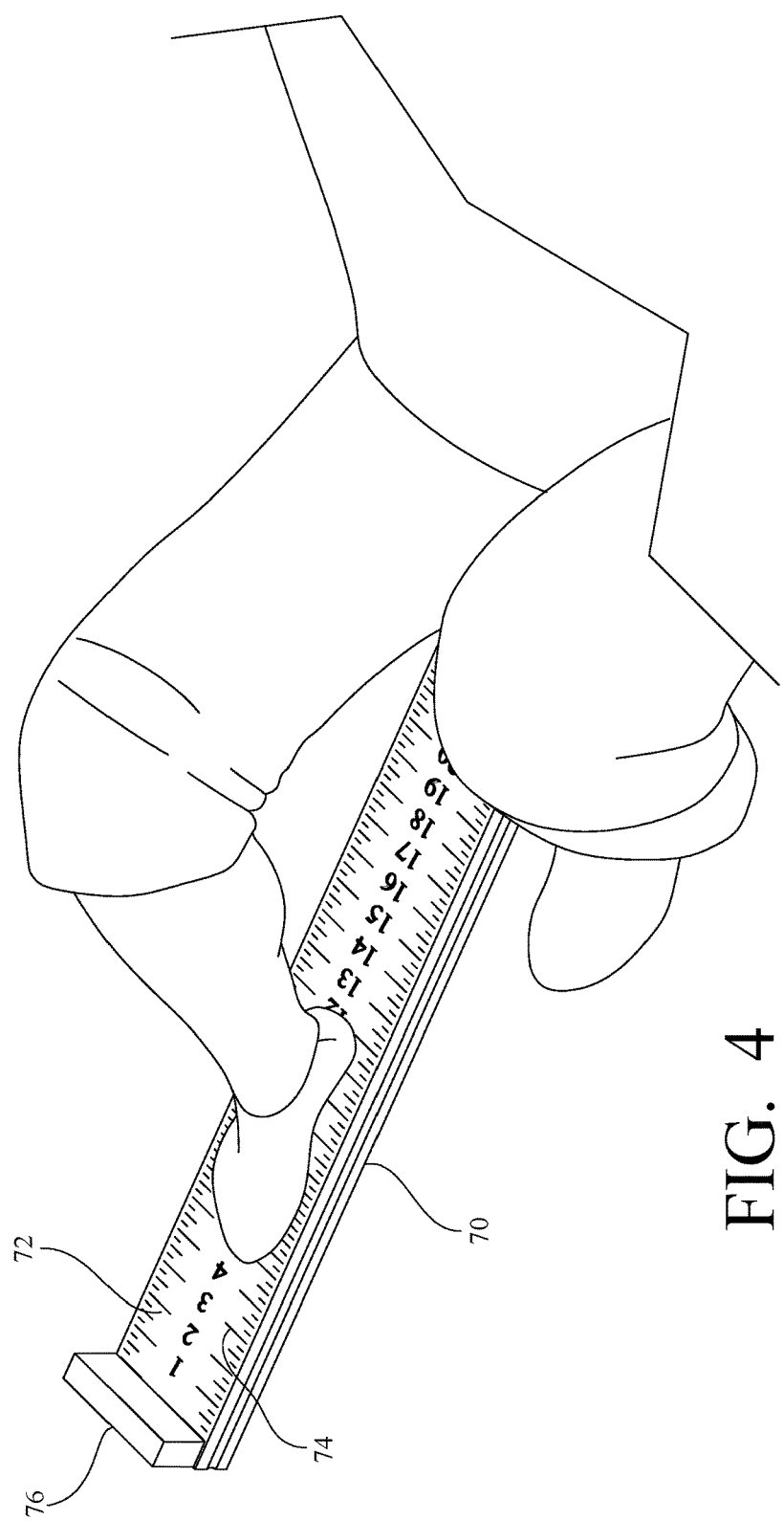
FIG. 4 is a perspective view that is substantially identical to FIG. 3, but with the patient bending the knee at maximum flexion.

Referring now to FIGS. 1, 3 and 4, in order to assess the knee flexion of an individual with the system of the present invention, a measurement of the patient's lower leg is first taken. Specifically, the lower leg measurement is taken from about the patient's ankle to about the central axis of rotation of the patient's knee. Similarly, an upper leg measurement is taken from about the central axis of rotation of the patient's knee to about the greater trochanter of the patient's femur.

Each of the adjustable legs 50, 60 is positioned relative to the goniometer 20 to represent the lower leg measurement and the upper leg measurement. Specifically, after loosening the clamping knob 40, the first adjustable leg 50 is slid relative to the goniometer 20, as facilitated by the central channel 54 of the first adjustable leg 50, until the indicia 56 on the first adjustable leg 50 that reflects the lower leg measurement is positioned adjacent to the axis hole 24 of the goniometer 20 (i.e., the position of the clamping knob 40). Similarly, the second adjustable leg 60 is slid relative to the goniometer 20, as facilitated by the central channel 64 of the second adjustable leg 60, until the indicia 66 on the second adjustable leg 60 that reflects the upper leg measurement is positioned adjacent to the axis hole 24 of the goniometer 20 (i.e., the position of the clamping knob 40).

Referring now to FIG. 3, the patient then sits down and positions his leg on the base board 70 with his heel against the heel stop 76. This is effectively a "zero flexion position." Of course, such a heel stop 76 is not required, and the patient may simply position their heel at the distal end of the base board 70 in the "zero flexion position." Regardless, and referring now to FIG. 4, the patient begins bending his or her knee, such that the foot slides along the upper surface 72 of the base board 70 until the knee is at maximum flexion, which in FIG. 4, is at about twelve inches. Maximum flexion can be achieved through either an active or passive heel slide. In either case, the linear position of the heel at maximum flexion is marked on the base board 70. Based on the indicia 74 on the base board 70, the measured linear distance traveled by the heel in maximum flexion may also be recorded for later reference.

In other embodiments, the base board may include a moveable member (not shown) slidably connected to the base board. The moveable member is either pushed back by the foot as it slides along the upper surface of the base board, or it is manually slid along the upper surface of the base board as the patient bends his or her knee. For example, U.S. Patent Publication No. 2016/0000369 is entitled "Measurement Device For Assessing Knee Movement" and describes such a base board that includes a moveable member. U.S. Patent Publication No. 2016/0000369 is incorporated herein by reference.

In either event, the patient may now stand up or otherwise move away from the base board 70. Referring once again to FIG. 1, the distal end 52 of the first adjustable leg 50 is positioned on the base board 70 at the indicia 74 representing the position of the heel at maximum flexion, or about twelve inches here. The distal end 62 of the second adjustable leg 60 is positioned on the base board 70 at a position representing the total leg length of the patient, or about 37 inches here. Of course, the total leg length is determined by adding the previously measured lower leg measurement to the previously measured upper leg measurement.

In positioning the respective distal ends 52, 62 of the first and second adjustable legs 50, 60 in this manner, the linear position (or length) of each adjustable leg 50, 60 is fixed relative to the goniometer, but the first and second adjustable legs 50, 60 can still be rotated relative to one another about the pivot pin 42; in other words, the angular distance between the first and second adjustable legs 50, 60 is altered to properly position the respective distal ends 52, 62 of the first and second adjustable legs 50, 60.

The two adjustable legs 50, 60 now approximately recreate the position of the patient's leg under maximum flexion, and once the position of the two adjustable legs 50, 60 is fixed relative to the goniometer 20, the goniometer 20 can be used to determine an angular measurement of the knee of the individual at maximum flexion. In particular, as mentioned above, the first and second legs 28, 30 of the goniometer 20 are aligned with the respective adjustable legs 50, 60, such that the indicia 26 on the central body portion 22 of the goniometer 20 allow for a measurement of the angle between the two adjustable legs 50, 60.

Advantageously, the system and method of the present invention provide a simple and accurate means of measuring the degree of flexion in the patient's knee. The patient is not required to hold his or her leg in maximum flexion while the angular measurement is taken. Rather, a simple linear measurement of maximum heel movement can be easily taken and later converted into an angular measurement by using the adjustable legs 50, 60 to simulate the patient's leg.

One of ordinary skill in the art will recognize that additional embodiments are also possible without departing from the teachings of the present invention. This detailed description, and particularly the specific details of the exemplary embodiment disclosed therein, is given primarily for clarity of understanding, and no unnecessary limitations are to be understood therefrom, for modifications will become obvious to those skilled in the art upon reading this disclosure and may be made without departing from the spirit or scope of the invention.

What is claimed is:
1. A system for assessing movement of a knee of an individual, comprising:
   a goniometer with a central body portion;
   a first adjustable leg mounted for movement with respect to the goniometer, such that a distance between a distal end of the first adjustable leg and the central body portion of the goniometer is adjustable to a first desired length, and, such that, in use, a position of a distal end of the first adjustable leg relative to the central body portion of the goniometer is adjusted to represent a lower leg measurement of the individual;
   a second adjustable leg mounted for movement with respect to the goniometer, such that a distance between a distal end of the second adjustable leg and the central body portion of the goniometer is adjustable to a second desired length, and, such that, in use, a position of a distal end of the second adjustable leg relative to the central body portion of the goniometer is adjusted to represent an upper leg measurement of the individual; and
   a base board marked with indicia to measure a linear position of a heel of the individual when the knee of the individual is at maximum flexion, wherein, in use, the distal end of the first adjustable leg and the distal end of the second adjustable leg are positioned on the base board, with the first adjustable leg and the second adjustable leg in a fixed linear position relative to the central body portion of the goniometer and representing an angular position of the knee of the individual at maximum flexion.

2. The system of claim 1, wherein the first adjustable leg includes indicia to reflect the lower leg measurement, and wherein the second adjustable leg includes indicia to reflect the upper leg measurement.

3. The system of claim 1, wherein the central body portion includes indicia that allow for an angular measurement of the first adjustable leg relative to the second adjustable leg.

4. The system of claim 1, wherein:
   the central body portion defines an axis hole;
   the first adjustable leg defines a channel along a longitudinal axis of the first adjustable leg, the channel defined by the first adjustable leg partially overlapping the axis hole;
   the second adjustable leg defines a channel along a longitudinal axis of the second adjustable leg, the channel defined by the second adjustable leg partially overlapping the axis hole; and
   a pivot pin extends through the axis hole defined by the central body portion, the channel defined by the first adjustable leg, and the channel defined by the second adjustable leg.

5. The system of claim 4, and further comprising:
   a clamping knob with the pivot pin extending from the clamping knob; and
   a nut connected to the pivot pin opposite the clamping knob, such that the central body portion, the first adjustable leg, and the second adjustable leg are positioned between the clamping knob and the nut.

6. The system of claim 1, wherein the distal end of the first adjustable leg is pointed.

7. The system of claim 1, wherein the distal end of the second adjustable leg is pointed.

8. The system of claim 1, and further comprising a heel stop attached to the base board at a distal end thereof, the heel stop defining a position of the heel of the individual when the knee is in a zero flexion position.

9. A system for assessing movement of a knee of an individual, comprising:
   a central body portion defining an axis hole;

a first adjustable leg defining a channel along its longitudinal axis, wherein the channel defined by the first adjustable leg partially overlaps the axis hole, with a pivot pin extending through the axis hole defined by the central body portion and the channel defined by the first adjustable leg, such that a linear position of the first adjustable leg relative to the central body portion is adjustable to set a distance between a distal end of the first adjustable leg and the central body portion of the goniometer at a first desired length; and a second adjustable leg defining a channel along its longitudinal axis, the channel defined by the second adjustable leg partially overlapping the axis hole, with the pivot pin extending through the axis hole defined by the central body portion and the channel defined by the second adjustable leg, such that a linear position of the second adjustable leg relative to the central body portion is adjustable to set a distance between a distal end of the second adjustable leg and the central body portion of the goniometer at a second desired length;

wherein the central body portion includes indicia that are used to determine an angular measurement between the first adjustable leg and the second adjustable leg.

10. The system of claim 9, and further comprising a base board marked with indicia on its upper surface, such that, when the distal end of the first adjustable leg and the distal end of the second adjustable leg are each positioned on the base board, a linear distance on the base board is translated into the angular measurement between the first adjustable leg and the second adjustable leg.

11. A method for assessing movement of a knee of an individual, comprising the steps of:

providing a goniometer with a central body portion, along with a first adjustable leg mounted for movement with respect to the goniometer such that a distance between a distal end of the first adjustable leg and the central body portion of the goniometer is adjustable to a first desired length, and a second adjustable leg mounted for movement with respect to the goniometer such that a distance between a distal end of the second adjustable leg and the central body portion of the goniometer is adjustable to a second desired length;

adjusting a position of the distal end of the first adjustable leg relative to the central body portion of the goniometer to represent a lower leg measurement of the individual;

adjusting a position of the distal end of the second adjustable leg relative to the central body portion of the goniometer to represent an upper leg measurement of the individual;

positioning the distal end of the first adjustable leg on a base board marked with indicia in a position that represents a measured position of a heel of the individual during flexion of the knee;

positioning the distal end of the second adjustable leg on the base board marked with indicia in a position that represents a length of a leg of the individual; and determining an angular measurement of the knee during flexion by referencing indicia on the goniometer.

\* \* \* \* \*